United States Patent [19]

Sestanj

[11] 4,447,452
[45] May 8, 1984

[54] N[(2-NAPHTHALENYL)THIOXOMETHYL]GLYCINE DERIVATIVES

[75] Inventor: Kazimir Sestanj, St. Laurent, Canada

[73] Assignee: Ayerst, McKenna & Harrison Inc., Montreal, Canada

[21] Appl. No.: 321,303

[22] Filed: Nov. 13, 1981

[30] Foreign Application Priority Data

Mar. 2, 1981 [CA] Canada ................................. 372024

[51] Int. Cl.³ .................... C07C 153/05; A61K 31/195
[52] U.S. Cl. ....................................... 424/319; 560/10; 560/56; 560/100; 562/427
[58] Field of Search .......................... 562/427; 424/319

[56] References Cited

U.S. PATENT DOCUMENTS 3,489,793  1/1970  Bertelli ................................. 562/450
3,619,196  11/1971 Iwama ................................... 96/100
3,821,383  6/1974  Sestanj et al. ........................ 424/258

OTHER PUBLICATIONS

Allinger, "Organic Chemistry", pp. 532–537 (1971).
D. Dvornik et al., Science, 182, 1146(1973).
M. J. Peterson et al., Metabolism, 28 (suppl. 1), 456 (1979).
A. Lawson and C. E. Searle, J. Chem. Soc., 1556 (1957).
V. I. Cohen et al., Chem. Abstr., 86, 189582f (1977).
J. Voss and W. Walter, Chem. Abstr., 70, 11306a (1969).
Chem. Abstr., 61, 4333f (1964).
Chem. Abstr., 73, 30644n (1970).

Primary Examiner—Michael L. Shippen
Attorney, Agent, or Firm—Arthur E. Wilfond

[57] ABSTRACT

Herein disclosed are N-[(2-naphthalenyl)thioxomethyl]glycine derivatives of the formula

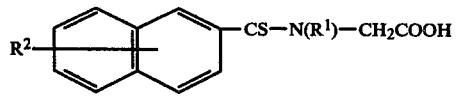

wherein $R^1$ is lower alkyl and $R^2$ is hydrogen, lower alkyl, lower alkoxy, halo or trifluoromethyl. The derivatives have aldose reductase inhibiting activity and are useful for treating diabetic complications.

9 Claims, No Drawings

N[(2-NAPHTHALENYL)THIOXOMETHYL]GLYCINE DERIVATIVES

RELATED APPLICATIONS

Related hereto are U.S. patent application Ser. No. 321,306, U.S. patent application Ser. No. 321,304, now U.S. Pat. No. 4,391,816 and U.S. patent application Ser. No. 321,300, now U.S. Pat. No. 4,391,825, all filed on the same date as this application.

This application relates to N-[(2-naphthalenyl)thioxomethyl]glycine derivatives, therapeutically acceptable salts thereof, a process for their preparation and to pharmaceutical compositions thereof. The derivatives have pharmacologic properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy and cataracts. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. Other compounds having a similar utility are the thioxo-1H-benz-[de]isoquinoline-2(3H)-acetic acid derivatives and the 1H-benz-[de]isoquinoline-2(3H)-acetic acid derivatives of U.S. patent applications Ser. No. 92,397, now U.S. Pat. No. 4,254,108 and 92,604, now U.S. Pat. No. 4,254,109 respectively, both filed Nov. 8, 1979. (S)-6-Fluoro-2,3-dihydrospiro(4H-1-benzopyran-4,4'-imidazolidine)-2',5'-dione (sorbinil) is still another compound that has received attention because of its aldose reductase inhibiting properties (see M. J. Peterson et al., Metabolism, 28 (Suppl. 1), 456 (1979). Accordingly, these compounds represent an important new approach for the treatment of diabetes mellitus.

The present application discloses novel N-[(2-naphthalenyl)thioxomethyl]glycine derivatives which are effective inhibitors of aldose reductase. These new derivatives are structurally quite different from the above noted aldose reductase inhibitors. Close prior art compounds, on a structural basis, appear to be a group of thioacylaminoacids, e.g. N-phenylthioxomethyl-N-methylglycine, prepared by A. Lawson and C. E. Searle, J. Chem. Soc., 1556 (1957) as part of a chemical investigation of the chemical properties of such compounds. The last mentioned compounds were prepared by thiobenzoylation of various amino acids with (thiobenzoylthio)acetic acid. An important structural difference between these compounds and the present derivatives is the different type of aromatic group substituted on the thione portion of the thioamide. Thioacylamides also have been reported [see Chem. Abstr., 86, 189582f (1977) for V. I. Cohen et al., Eur. J. Med. Chem., 5, 480 (1976) and Chem. Abstr., 70, 11306a (1969) for von J. Voss and W. Walter, Justus Leibigs Ann. Chem., 716, 209 (1968)]. The structures of the thioacylamides of Cohen et al and Voss et al differ from the structure of the present derivatives by having at least a different type of N-substitution. Other prior art compounds are N-[(1-and 2-naphthalenyl)carbonyl]glycine derivatives, e.g. see Chem. Abstr., 61, 4333f (1964) for E. Cioranescu et al., Rev. Chim. Acad. Rep. Populaire Roumaine, 7(2), 755 (1962); J. W. Bunting et al., Biochim. Biophys. Acta., 524, 142 (1978); and Chem. Abstr., 73, 30644n (1970) for I. Masakuni et al., Ger. Offen. 1,953,372, published May 21, 1970. The latter compounds are distinguished from the compounds of the present invention by being acylaminoacids and not thioacylaminoacids.

SUMMARY OF THE INVENTION

The N-[(2-naphthalenyl)thioxomethyl]glycine derivatives of this invention are represented by formula I

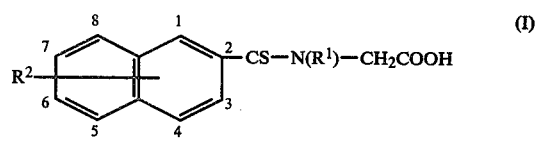

wherein $R^1$ is lower alkyl, and $R^2$ is hydrogen or a lower alkyl, lower alkoxy, halo or trifluoromethyl substituent on the naphthalene ring, or a therapeutically acceptable salt thereof with an organic or inorganic base.

A group of preferred compounds is represented by formula I wherein $R^2$ is a halo substituent on the naphthalene ring.

A most preferred group of compound is represented by formula I wherein $R^2$ is a halo substituent at positions 5 or 6 of the naphthalene ring.

The compounds of formula I can be prepared by a process wherein a corresponding ester of the compound of formula I is hydrolyzed. In a preferred embodiment, the ester has the formula

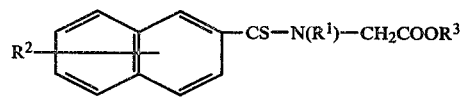

wherein $R^3$ is lower alkyl or ar(lower)alkyl and $R^1$ and $R^2$ are as defined herein.

A method is provided for preventing or relieving diabetes mellitus associated complications in a diabetic mammal by administering to said mammal an prophylactic or alleviating amount of the compound of formula I or a therapeutically acceptable salt thereof with an organic or inorganic base.

The compound of formula I, or a therapeutically acceptable salt thereof with an organic or inorganic base, when admixed with a pharmaceutically acceptable carrier, forms a pharmaceutical composition which can be used according to the preceding method.

DETAILED DESCRIPTION OF THE INVENTION

The term "lower alkyl" as used herein means a straight chain alkyl radical containing from one to four carbon atoms or a branched chain alkyl radical containing three or four carbon atoms and includes methyl, ethyl, propyl, 1-methylethyl, butyl, 2-methylpropyl and 1,1-dimethylethyl. Preferred lower alkyl radicals contain one to three carbon atoms.

The term "lower alkoxy" as used herein means a straight chain alkoxy radical containing from one to six carbon atoms, preferably one to three carbon atoms, or a branched chain alkoxy radical containing three or four carbon atoms, and includes methoxy, ethoxy, 1-methylethoxy, butoxy and hexanoxy.

The term "halo" as used herein means halogens and includes fluoro, chloro, bromo and iodo.

The term "ar" as used mean an aromatic radical containing at least one benzene ring. The preferred aromatic radical is phenyl.

The compounds of formula I form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or low polarity, for example, ethanol, methanol, ethyl acetate, diethyl ether and benzene. At least an equivalent amount of the amine corresponding to the desired cation is than added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2-7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2-7.6 containing a pharmaceutically acceptable buffer.

The dosage of the present therapeutic agents will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration a 0.05–0.2% solution may be administered dropwise to the eye. The frequency of instillation varies with the subject under treatment from a drop every two or three days to once daily. For oral or parenteral administration a preferred level of dosage ranges from about 2 to about 200 mg per kilo of body weight per day, although aforementioned variations will occur. However, a dosage level that is in the range of from about 10 to about 50 mg per kilo of body weight per day is most satisfactory.

Unit dosage forms such as capsules, tablets, pills and the like may contain from about 25 to about 250 mg of the active ingredients of this invention, dependent on the type of unit dosage, preferably with a significant quantity of a pharmaceutical carrier. Thus, for oral administration, capsules can contain from between about 25 to about 250 mg of the active ingredients of this invention with or without a pharmaceutical diluent. Tablets, either effervescent or noneffervescent, can contain between about 25 to 250 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

Syrups or elixirs suitable for oral administration can be prepared from water soluble salts, for example, sodium N-[(5-bromo-2-naphthalenyl)thioxomethyl]-N-glycinate, and may advantageously contain glycerol and ethyl alcohol as solvents or preservatives.

The compound of formula I, or a therapeutically acceptable salt thereof, also can be used in combination with insulin or oral hypoglycemic agents to produce beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compound of formula I, or a therapeutically acceptable salt thereof, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 34 ed., Medical Economics Co., Oradell, N.J., U.S.A., 1980. When used in combination, the compound of formula I, or its therapeutically acceptable salt, is administered as described previously. The compound of formula I, or its therapeutically acceptable salt, can be administered with the oral hypoglycemic agent in the form of a pharmaceutical composition comprising effective amounts of each agent.

The aldose reductase inhibiting effects of the compounds of formula I and their pharmaceutically acceptable salts with organic or inorganic bases can be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

The following results were obtained when the compounds of this invention were evaluated in the above in vitro test.

| Compound of Formula I | | % Inhibition at Different Molar Concentrations (in vitro) | | |
|---|---|---|---|---|
| $R^1$ | $R^2$ | $10^{-5}$ | $10^{-6}$ | $10^{-7}$ |
| $CH_3$ | 5-Br | 87 | 70 | 21 |
| $CH_3$ | 6-Br | 84 | 60 | 19 |

PROCESS

The compounds of this invention can be prepared by a process which is illustrated by the following reaction scheme in which $R^1$ and $R^2$ are as defined hereinbefore and $COOR^3$ is an ester group which, for example, may be a lower alkyl or an ar(lower)alkyl [i.e. $R^3$ is lower alkyl or ar(lower)alkyl].

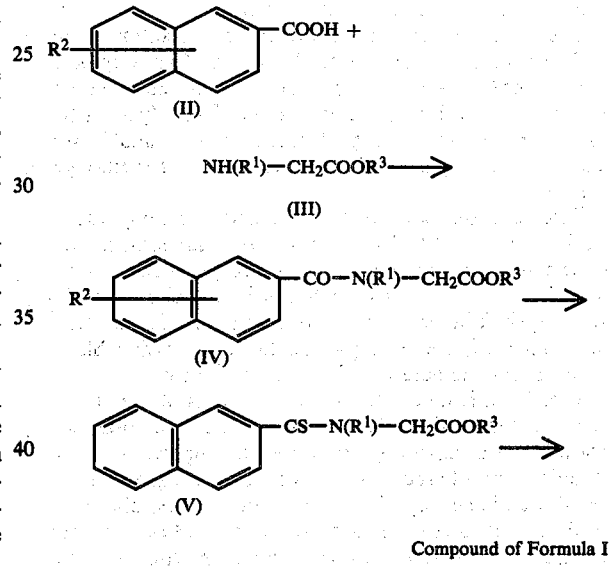

Compound of Formula I

The starting materials of formula II are known or can be prepared by known methods. For example, see "Elsevier's Encyclopaedia of Organic Chemistry", F. Radt, Ed., Series III, Vol. 12B, Elsevier Publishing Co., Amsterdam, 1953, pp 3963–4473.

With reference to the reaction scheme, the starting material of formula II is coupled with the aminoacid ester of formula III to obtain the amidoester of formula IV by the "carboxyl activation" coupling procedure. Descriptions of carboxyl-activating groups are found in general textbooks of peptide chemistry; for example K. D. Kopple, "Peptides and Amino Acids", W. A. Benjamin, Inc., New York, 1966, pp. 45–51, and E. Schröder and K. L/üke, "The Peptides"; Vol. 1, Academic Press, New York, 1965, pp. 77–128. Examples of the activated form of the terminal carboxyl are the acid chloride, acid bromide, anhydride, azide, activated ester, or O-acyl urea of a dialkylcarbodiimide. Preferred activated forms of the carboxyl are the acid chloride or the 1-benzotriazolyl, 2,4,5-trichlorophenyl or succinimido activated esters.

Thereafter, the amido ester of formula IV is reacted under anhydrous conditions with about two to five molar equivalents of phosphorus pentasulfide in an inert solvent, e.g. xylene or toluene, to obtain the corresponding thioxoester of formula V. This reaction is performed conveniently at temperatures ranging from 80° to about 150° C. and at times ranging from 20 minutes to four hours. This reaction also can be performed in the presence of an organic base for instance, N-ethyl morpholine, triethylamine or pyridine.

Finally, the thioxoester of formula V is hydrolyzed with a hydrolyzing agent to give the corresponding product of formula I. Generally speaking, this conversion is most conveniently performed by employing a base as the hydrolyzing agent. The hydrolysis is performed in the presence of sufficient water, followed by acidification of the reaction mixture to yield the desired acid. However, it should be understood that the manner of hydrolysis for the process of this invention is not intended to be limited to basic hydrolysis, since hydrolysis under acidic conditions and other variations, for example, treatment with lithium iodide in collidine (see L. F. Fieser and M. Fieser, "Reagents for Organic Synthesis", John Wiley and Sons, Inc., New York, 1969, pp. 615-617), are also applicable. For the hydrolysis of tert butyl esters, acid hydrolysis is preferred.

For basic hydrolysis, a preferred embodiment involves subjecting the ester to the action of a strong base, for example, sodium or potassium hydroxide, in the presence of sufficient water to effect hydrolysis of the ester. The hydrolysis is performed using a suitable solvent, for example, methanol, ethanol or 2-methoxyethanol.

The reaction mixture is maintained at a temperature of from about 25° to 100° C. or at the reflux temperature of the solvent employed until hydrolysis occurs. Usually from 10 minutes to 6 hours is sufficient for this hydrolysis. The reaction mixture is then rendered acidic with an acid, for example, acetic acid, hydrochloric acid or sulfuric acid to release the free acid.

Finally, it is noted that the compounds of this invention, represented by formula I, can exist in rotameric forms. More explicitly, mesomerism imparts a partial double bond character to the carbon-nitrogen bond of the thioamide group. This partial double bond character leads to restricted rotation about the carbon nitrogen bond giving rise to cis and trans rotamers, the restricted rotation being augmented by the bulkiness of neighboring groups. Interconversion of the rotamers is possible and is dependent on the physical environment. As evidenced by its physical properties, the thermodynamically more stable rotamer exists exclusively in the crystalline state of the compound and is the predominant isomer present in equilabrated solutions. Furthermore, the more stable rotamer is the more pharmacologically active. The less stable rotamer can be separated from the more stable rotamer by high performance liqid chromatography or by thin layer chromatography. The rotameric forms are included within the scope of this invention. For brevity, the compounds of this invention, including their rotameric forms, are referred to herein as compounds of formula I.

The following examples illustrate further this invention.

EXAMPLE 1

N-[(6-Bromo-2-naphthalenyl)carbonyl]-N-methylglycine Methyl Ester (IV, $R^1$ and $R^3$=$CH_3$ and $R^2$=6-Br)

The title compound can be prepared by two procedures designated as procedure A and procedure B below. The starting material of formula II used in each of these procedures is prepared as follows: A sodium hypochlorite solution was prepared by introducing chlorine gas (11.2 g) into a solution of NaOH (15.3 g) in 200 ml of ice water. Solid (6-bromo-2-naphthalenyl)ethanone [9.5 g, 38.1 mmoles, prepared according to the procedure of R. B. Girdler et al., J. Chem. Soc. (C), 518 (1966)] was added to the stirred sodium hypochlorite solution at 0° C. and then the mixture was heated on a steam bath for 1 hr. The precipitate was removed by filtration. Sodium metabisulfite (5 g) was added to the cooled (0° C.) filtrate. The mixture was adjusted to pH 5 with concentrated HCl. The precipitate was collected and dried. The collected precipitate was crystallized from boiling ethanol by the addition of water to afford 5.5 g (two crops) of 6-bromo-2-naphthalenecarboxylic acid; mp 288°-290° C.; NMR (CDCl$_3$) δ 7.68 (2d, J=8 Hz, J$_2$=2 Hz, 1H), 7.97 (m, 2H), 8.05 (d, J=8 Hz, 1H), 8.25 (d, H), 8.58 (d, 1H), IR (CHCl$_3$), 2800, 1680, 1625, 1567 cm$^{-1}$; UVλmax (EtOH) 333 nm (ε1080), 323 (880), 317 (1020), 286 (9040), 237 (54,350).

Procedure A for preparing the title compound:

A suspension of 6-bromo-2-naphthalenecarboxylic acid (5.37 g, 21.4 mmoles, a starting material of formula II) in thionyl chloride (54 ml) containing 5 drops of dimethylformamide (DMF) was refluxed for 30 min. The mixture was evaporated to dryness under reduced pressure. The residue was dissolved in dry pyridine (54 ml). N-Methylglycine hydrochloride (2.8 g, 20.2 mmoles), a starting material of formula III, was added to the solution. The resulting mixture was stirred at 20°-22° C. for 2 hr and then refluxed for 3 hr. The mixture was evaporated to dryness. The residue was dissolved in ethyl acetate (600 ml) and water (100 ml). After shaking the mixture and separating the two layers, the aqueous layer was extracted with more ethyl acetate. The combined organic extracts were washed with 2 N aqueous HCl, brine and water, dried (MgSO$_4$) and evaporated to dryness. The residue (5.6 g) was crystallized from ethanol to give 3.4 g of the title compound; mp 103°-105° C.; NMR (CDCl$_3$) δ 2.75 (s, 3H), 3.08 (s, 3H), 4.25 (s, 2H), 7.30-8.20 (m, 6H); IR (CHCl$_3$) 1738, 1630, 1580 cm$^{-1}$; UVλmax (EtOH) 280 nm (ε6,980), 273 (6,720), 232 (64,740); Anal Calcd: C, 53.59% H, 4.20% N, 4.17%; Found: C, 53.41% H, 4.29% N, 4.27%.

Procedure B for preparing the title compound

A stirred mixture of the starting material of formula II, 6-bromo-2-naphthalenecarboxylic acid (12.8 g, 52 mmoles), and 1-hydroxybenzotrizole (HOBt, 7.0 g, 52 mmoles) in DMF (200 ml) was cooled to 0° C. N,N-dichlohexylcarbodiimide (DCC, 10.6 g, 52 mmoles) in DMF (30 ml) was added to the mixture. The resulting mixture was stirred at 0° C. for 30 min and at 20° C. for 1 hr and then cooled again to 0° C. N-Methylglycine methyl ester hydrochloride (7.25 g, 52 mmoles), followed by N-ethylmorpholine (6.7 ml, 52 mmoles), were added to the cooled mixture. The mixture was stirred for 30 min at 0° C. and then for 18 hr at 20° C. Thereafter, the mixture was filtered and concentrated to dryness under reduced pressure. The residue was subjected to chromatography on 325 g of silica gel using ethyl acetate-hexane (1:1) as the eluant. The pure fractions were pooled to yield 10.5 g of product which was recrystallized from ethyl acetate to give the title compound, identical to the product of procedure A of this example.

EXAMPLE 2

N-[(6-Bromo-2-naphthalenyl)thioxomethyl]-N-methylglycine Methyl Ester (V, $R^1$ and $R^3 = CH_3$ and $R^2 = 6$-Br)

To a stirred solution of N-[(6-bromo-2-naphthalenyl)carbonyl]-N-methylglycine methyl ester (3.2 g, 9.5 mmoles, described in Example 1) in dry pyridine (20 ml), phosphorus pentasulfide 2.65 g, 11.9 mmoles) was added portionwise. The mixture was stirred and refluxed for 4.5 hr and then poured into 300 ml of water (caution: evolution of copious quantities of $H_2S$). The mixture was stirred and cooled to 20° to 22° C. (room temperature) and then extracted with chloroform. The extract was washed with 2 N aqueous HCl solution, 5% aqueous sodium bicarbonate solution and water, dried ($MgSO_4$), filtered and evaporated to dryness. The residue was crystallized from ethanol to give 1.6 g of the title compound; mp 125°–127° C.; NMR ($CDCl_3$) δ 3.22 and 3.58 (2s, 3H), 2.70 and 3.81 (2s, 3H), 4.18 and 4.86 (2s, 3H), 7.25–8.10 (m, 6H); IR ($CHCl_3$) 1743, 1619, 1584 cm$^{-1}$; UVλmax (EtOH) 284 nm (ε15,730), 276 (15,590), 246 (43,090), 219 (43,160).

By following serially the procedures of Examples 1 and 2 and using the appropriate starting material of formula II instead of 6-bromo-2-naphthalenecarboxylic acid, together with the appropriate starting material of formula III, other compounds of formula V are obtained. For example, by using 5-bromo-2-naphthalenecarboxylic acid, described by H. Goldstein et al., Helv. Chim. Acta, 21, 62 (1938), as the starting material of formula II and following serially the procedures, N-[(5-bromo-2-naphthalenyl)thioxomethyl]-N-methylglycine methyl ester is obtained via the intermediate N-[(5-bromo-2-naphthalenyl)carbonyl]-N-methyl glycine methyl ester.

EXAMPLE 3

N-[(6-Bromo-2-naphthalenyl)thioxomethyl]-N-methylglycine (I, $R^1 = CH_3$ and $R^2 = 6$-Br)

N-[(6-Bromo-2-naphthalenyl)thioxomethyl]-N-methylglycine methyl ester (1.58 g, 4.49 mmoles, described in Example 2) was suspended in methanol (16 ml). An 1 N aqueous NaOH solution (5.5 ml) was added to the suspension. The mixture was stirred at room temperature (20°–22° C.) for 2 hr. Chloroform (3.6 ml) and additional 1 N aqueous NaOH solution (2 ml) were added and the mixture was stirred for an additional 18 hr at room temperature. The mixture was made neutral with 2 N aqueous HCl solution and then evaporated to dryness. The residue was suspended in water (25 ml). The suspension was made acidic with concentrated HCl. The resulting precipitate was collected, washed with water, dried and recrystallized from ethyl acetate/hexane to give 1.19 g of the title compound; mp 173°–175° C.; NMR (DMSO-$d_6$) δ 3.25 and 3.6 (2s, 3H), 4.25 and 4.9 (2s, 2H), 7.2–7.9 (m, 6H); IR (Nujol*) 2900, 1720 cm$^{-1}$; UVλmax (EtOH) 287 nm (ε15,590), 276 (15,490), 246 (43,400), 221 (44,310); Anal Calcd: C, 49.72% H, 3.58% N, 4.14%; Found: C, 50.02% H, 3.62% N, 4.22%.

\* Nujol is a trademark for a brand of white mineral oil.

In the same manner but replacing N-[(6-bromo-2-naphthalenyl)thioxomethyl]-N-methylglycine with an equivalent amount of another ester of formula V, other compounds of formula I are obtained. For example, replacement with N-[(5-bromo-2-naphthalenyl)thioxomethyl]-N-methylglycine methyl ester, described in the preceding example, gave N-[(5-bromo-2-naphthalenyl)thioxomethyl]-N-methylglycine; mp 180° C. (dec); NMR (DMSO-$d_6$) δ 3.2 and 3.55 (2s, 3H), 4.25 and 4.85 (2s, 2H), 7.75 (m, 6H); IR (Nujol*) 2900, 1690, cm$^{-1}$; UVλmax (EtOH) 276 nm (ε15,900), 247 (32,470), 319 (42,720); Anal Calcd: C, 49.72% H, 3.58% N, 4.14%; Found: C, 50.04% H, 3.75% N, 4.25%.

\* Nujul is a trademark for a brand of white mineral oil.

We claim:

1. A compound of formula I

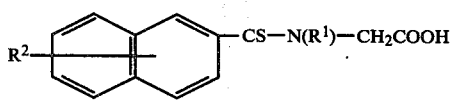

wherein $R^1$ is lower alkyl, and $R^2$ is hydrogen or a lower alkyl, lower alkoxy, halo or trifluoromethyl substituent on the naphthalene ring, or a therapeutically acceptable salt thereof with an organic or inorganic base.

2. The compound of claim 1 wherein $R^2$ is a halo substituent on the naphthalene ring.

3. The compound of claim 1 wherein $R^2$ is a halo substituent at position 5 or 6 of the naphthalene ring.

4. N-[(6-Bromo-2-naphthalenyl)thioxomethyl]-N-methylglycine, as claimed in claim 1.

5. N-[(5-Bromo-2-naphthalenyl)thioxomethyl]-N-methylglycine, as claimed in claim 1.

6. A pharmaceutical composition for preventing or relieving diabetic complications in a diabetic mammal which comprises a compound of claim 1, or a therapeutically acceptable salt thereof with an organic or inorganic base, and a pharmaceutically acceptable carrier.

7. The pharmaceutical composition of claim 6 which also comprises an oral hypoglycemic agent.

8. A method of preventing or relieving diabetic complications in a diabetic mammal which comprises administering to said mammal an alleviating or prophylactic amount of a compound of claim 1, or a therapeutically acceptable salt thereof with an organic or inorganic base.

9. The method of claim 8 in which the administration of the compound of claim 1 is performed simultaneously or sequentially with the administration of an effective blood glucose lowering amount of insulin or an oral hypoglycemic agent.

* * * * *